(12) United States Patent
Shaviv

(10) Patent No.: US 9,827,136 B2
(45) Date of Patent: Nov. 28, 2017

(54) DROGUE-LIKE MENSES COLLECTION DEVICE

(71) Applicant: Gals Bio Ltd., Tel-Aviv (IL)

(72) Inventor: Hilla Shaviv, Mevasseret Zion (IL)

(73) Assignee: Gals Bio Ltd., Tel-Aviv (IL)

( * ) Notice: Subject to any disclaimer, the term of this patent is extended or adjusted under 35 U.S.C. 154(b) by 320 days.

(21) Appl. No.: 13/933,307

(22) Filed: Jul. 2, 2013

(65) Prior Publication Data

US 2014/0012216 A1  Jan. 9, 2014

Related U.S. Application Data

(60) Provisional application No. 61/669,137, filed on Jul. 9, 2012.

(51) Int. Cl.
| | |
|---|---|
| *B29C 39/00* | (2006.01) |
| *A61M 29/00* | (2006.01) |
| *A61F 13/20* | (2006.01) |
| *A61F 5/455* | (2006.01) |
| *A61F 6/08* | (2006.01) |

(52) U.S. Cl.
CPC .............. *A61F 5/4553* (2013.01); *A61F 6/08* (2013.01); *Y10T 29/49826* (2015.01)

(58) Field of Classification Search
CPC ................................ B29C 39/00; A61F 5/4553
See application file for complete search history.

(56) References Cited

U.S. PATENT DOCUMENTS

| | | | | |
|---|---|---|---|---|
| 3,841,333 | A * | 10/1974 | Zalucki .................. | A61F 5/4553 604/330 |
| 5,295,984 | A | 3/1994 | Contente et al. | |
| 6,168,609 | B1 * | 1/2001 | Kamen .................. | A61F 5/4553 600/573 |
| 6,332,878 | B1 * | 12/2001 | Wray ........................ | A61F 6/08 128/830 |
| 2007/0088623 | A1 * | 4/2007 | Chin ....................... | G06Q 30/02 705/26.7 |

* cited by examiner

*Primary Examiner* — Philip R Wiest
*Assistant Examiner* — Sara Sass

(57) ABSTRACT

A disposable catamenial device for the collection of menses discharge of the female human, including: a flexible resilient menstrual cup (MC), which includes: at least two resilient ribs extending inwardly from the inner surface of the MC base; an elastic rim frame connected to the top of the ribs; a reservoir bag connected to the rim in a sealed manner for collecting the menstrual fluid; and a withdrawal string connected to the cup bottom for enabling the extraction of said MC from the vagina. The MC has a drogue like structure comprising at least two flexible ribs having arcuate vertical struts (AVS) structure connected to a flat base. The ribs are connected to the elastic rim frame with at least two flexible arcuate horizontal struts (AHS).

32 Claims, 3 Drawing Sheets

DROGUE-LIKE MENSES COLLECTION DEVICE

FIELD OF INVENTION

Figure 1:
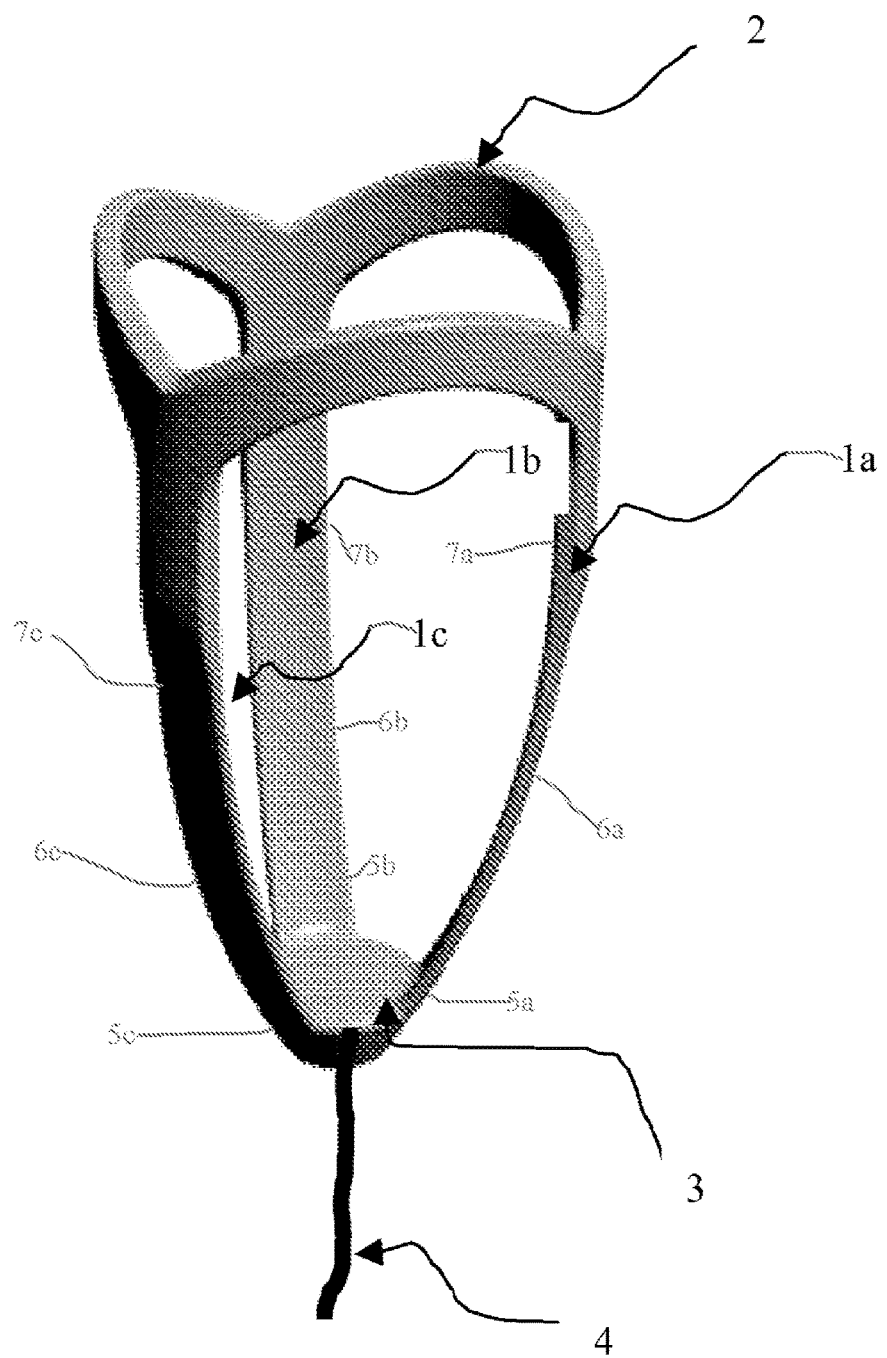

This present invention relates to a obstetrical-gynecological device including an applicator for collection of the menses of the human female, more specifically to an inter vaginal device having a drogue-like structure appropriate for collecting menstrual secretion.

BACKGROUND

Various devices have been devised for the purpose of collecting or blocking menstrual flow. These include high absorbency tampons, pads, menstrual cups that abut the walls of the vagina and block the passage of fluids from the cervix to the exit of the vagina, or other internally placed devices having a diaphragm-like structure.

U.S. Pat. No. 6,332,878 discloses a device for collecting menstrual flow which has a cup shaped to fit over the cervix and has an attached pouch defining a reservoir that contains an absorbent material. The device further includes a port having a fabric cover permits menstrual flow from the uterus to pass into the reservoir. The device described is delivered into the vagina using an applicator. The device described is shaped to automatically fit into and remain in position over the cervix after the device is ejected from the applicator.

U.S. Pat. No. 5,295,984 discloses a vaginal discharge collection device is formed of an elastomeric rim and a flexible film reservoir. The rim has a generally rectangular cross section and forms a collection space for collecting vaginal discharge. The reservoir may be collapsible so as to be substantially enclosed within the rim when the device is being used. Advantageously, the rim and the reservoir are arranged such that compressing diametrically opposed portions of the rim toward each other causes a leading portion of the rim to dip downwardly to facilitate insertion of the device. The device is ergonomically constructed so as to be convenient to use, comfortable to wear internally, and reliable.

The devices known in the art may allow leakage and hygiene difficulties when disarranged by the user's movement or improperly worn or inserted or ejected. Furthermore they increase the risk of toxic shock syndrome and also reusable and must be washed after use. There is therefore a long unmet need for improved device for collecting and containing menstrual flow which will overcome the above problems, methods and devices.

SUMMARY

The catamenial device herein disclosed is designed to meet this need. It is therefore an object of the present invention to disclose a disposable catamenial device for the collection of menses discharge of the female human, comprising: a flexible resilient menstrual cup (MC), comprising: (i) at least three resilient ribs extending inwardly from the inner surface of the MC base; (ii) an elastic rim frame connected to the top of the ribs; (iii) a reservoir bag connected to the ribs in a sealed manner for collecting the menstrual fluid; and (iv) a withdrawal string connected to the cup bottom for enabling the extraction of the MC from the vagina.

The MC has a drogue like structure comprising at least three flexible ribs having arcuate vertical struts (AVS) structure connected to a flat base; the ribs connected with elastic rim frame comprising at least three flexible arcuate horizontal struts (AHS), further wherein the AHS has a curvature less than the curvature of the AVS allowing easier deployment of the MC resulting in low resistance when inserted and substantial resistance when drawn from the vaginal cavity.

It is one object of the present invention to provide a disposable catamenial device for the collection of menses discharge of the female human, comprising: a flexible resilient menstrual cup (MC), comprising: (i) at least three resilient ribs extending inwardly from the inner surface of the MC base; (ii) an elastic rim frame connected to the top of the ribs, (iii) a reservoir bag connected to the ribs in a sealed manner for collecting the menstrual fluid; and (iv) a withdrawal string connected to the cup bottom for enabling the extraction of the MC from the vagina;

wherein the disposable catamenial device comprises biodegradable materials and further comprises an applicator for delivering the MC into the vaginal canal and extracting the MC; further wherein the reservoir bag comprises an absorbent element located along the bag walls preventing spill and leakage during extraction of the MC. It is another object of the present invention to provide the disposable catamenial device as defined above, wherein the AVS and AHS structure provides an additional spring-like resilience for facilitating semi-automatic deployment of the device to a sealing position within the vagina cavity.

It is another object of the present invention to provide the disposable catamenial device as defined above, wherein the rim functions as a spring such that when ejected outside the applicator, the rim returns to its original shape and the MC is opened within the potential vaginal cavity.

It is another object of the present invention to provide the disposable catamenial device as defined above, wherein the rim resilient structure and elasticity enables the MC to be positioned with in the vagina in a sealed manner such that the MC comprising the collected fluid is held inside the vagina.

It is another object of the present invention to provide the disposable catamenial device as defined above, wherein the rim is formed of an injection molded thermoplastic rubber.

It is another object of the present invention to provide the disposable catamenial device as defined above, wherein the MC has a drogue-like structure such that it provides substantial resistance when dragged from the vagina cavity and allows easier deployment.

It is another object of the present invention to provide the disposable catamenial device as defined above, wherein the MC may further have a funnel-like structure, a cone-like structure, an umbrella-like structure or any combination thereof.

It is another object of the present invention to provide the disposable catamenial device as defined above, wherein the reservoir is collapsible so as to be substantially enclosed within the rim during use.

It is another object of the present invention to provide the disposable catamenial device as defined above, wherein the applicator comprises two tubular insertion members having hollow cylinder shape while one has a diameter smaller than the other such that the smaller cylinder is inserted into the larger cylinder.

It is another object of the present invention to provide the disposable catamenial device as defined above, wherein the ribs have a parallel or vertical structure.

It is another object of the present invention to provide the disposable catamenial device as defined above, wherein the ribs are connected in an arch shape resulting a structure of a small elastic cup shape such that the MC will collapse into the applicator easily.

It is another object of the present invention to provide the disposable catamenial device as defined above, wherein the withdrawal string may further have an elongated tube shape.

It is another object of the present invention to provide the disposable catamenial device as defined above, wherein the withdrawal string part is used in order to extract the device from the vaginal cavity.

It is another object of the present invention to provide the disposable catamenial device as defined above, wherein the reservoir bag is adapted as a thin membrane which is connected to the ribs in a sealed manner for collecting menstrual fluid.

It is another object of the present invention to provide the disposable catamenial device as defined above, wherein the reservoir bag is made of elastic material or non-elastic material.

It is another object of the present invention to provide the disposable catamenial device as defined above, wherein the an absorbent element is made from absorbing material selected from a group consisting of: natural fibers, synthetic fibers, fluff pulp, needle-punched engineered absorbents, fiber tows, tow webs, cellulosic sponge materials, superabsorbent materials, materials which forms a gel upon contact with moisture, and combinations thereof.

It is another object of the present invention to provide the disposable catamenial device as defined above, wherein the disposable catamenial device for the collection of menses discharge of the female human, complies with FDA regulation pertaining to Obstetrical and Gynecological Devices.

It is another object of the present invention to provide the disposable catamenial device as defined above, wherein the disposable catamenial device complies with FDA class II performance standards It is another object of the present invention to provide the disposable catamenial device as defined above, wherein the disposable catamenial device meets FDA biocompatibility standards for prevention of adverse tissue reaction.

It is another object of the present invention to provide the disposable catamenial device as defined above, wherein the absorbent element complies with absorbency ratings selected from the group consisting of: 6 grams and under, 6 to 9 grams, 9 to 12 grams, 12 to 15 grams or 15-18 grams.

It is one object of the present invention to provide a method of manufacturing a device for containing menstrual flow of a female human comprising the steps of: (a) molding at least three longitude arch-like ribs made of flexible material in a drogue configuration to a flat base, (b) molding the ribs to at least three horizontal arcuate struts resulting a port having a resilient rim for leading menstrual flow discharged from the cervix to pass through the cup, (c) attaching a reservoir bag comprising an absorbent material, (d) contacting the drogue to the bag so as to define an intra vaginal reservoir for receiving and containing menstrual flow that enters the reservoir through the port; (e) fusing the bag to the drogue's ribs, and (f) attaching a withdrawal string to the flat base. The molding ribs results arcuate vertical struts (AVS) structure connected to a flat base; the ribs connected with elastic rim frame comprising at least three flexible arcuate horizontal struts (AHS), further wherein the AHS has a curvature less than the curvature of the AVS allowing easier deployment of the MS resulting in low resistance when inserted and substantial resistance when drawn from the vaginal cavity.

It is one object of the present invention to provide a method of capturing and containing the menstrual flow of a female human being comprising the steps of:
(a) providing a disposable catamenial device for the collection of menses discharge of the human female comprising:
a menstrual cup (MC), comprising:
(i) at least three resilient ribs extending inwardly from the inner surface of the MC base, (ii) an elastic rim frame connected to the top of the ribs, (iii) a reservoir bag connected to the ribs in a sealed manner for collecting the menstrual fluid, and (iv) a withdrawal string connected to the cup bottom for enabling the extraction of the MC from the vagina,
(b) providing an applicator, (c) placing in an end of an applicator the a disposable catamenial device, (d) inserting the end of the applicator into the vagina, (e) releasing the device from the end of the applicator whereby the device automatically seats itself within the vagina cavity, and (f) withdrawing the applicator from the vagina.

The disposable catamenial device comprises biodegradable materials and further comprises an applicator for delivering the MC into the vaginal canal and extracting the MC, further wherein the reservoir bag comprises an absorbent element located along the bag walls preventing spill and leakage during extraction of the MC.

It is another object of the present invention to provide the method as defined above, wherein the method of manufacturing a device for containing menstrual flow of a female human, complies with cGMP and QS.

It is another object of the present invention to provide the method as defined above, wherein the rim functions as a spring such that when ejected outside the applicator, the rim returns to its original shape and the MC is opened within the potential vaginal cavity.

It is another object of the present invention to provide the method as defined above, wherein the rim having a resilient structure and elasticity characters enables the MC to be positioned with in the vagina in a sealed manner such that the MC comprising the collected fluid is held inside the vagina.

It is another object of the present invention to provide the method as defined above, wherein the device for containing menstrual flow of a female human structure provides an additional spring-like resilience for facilitating semi-automatic deployment of the device to a sealing position within the vagina cavity.

It is another object of the present invention to provide the method as defined above, wherein the rim is formed of an injection molded thermoplastic rubber.

It is another object of the present invention to provide the method as defined above, wherein the MC has a drogue-like structure such that it provides substantial resistance when dragged from the vagina cavity and allows easier deployment.

It is another object of the present invention to provide the method as defined above, wherein the MC may further have a funnel-like structure, a cone-like structure, an umbrella-like structure or any combination thereof.

It is another object of the present invention to provide the method as defined above, wherein the reservoir bag is collapsible so as to be substantially enclosed within the rim during use.

It is another object of the present invention to provide the method as defined above, wherein the applicator comprises two tubular insertion members having hollow cylinder shape while one has a diameter smaller than the other such that the smaller cylinder is inserted into the larger cylinder.

It is another object of the present invention to provide the method as defined above, wherein the ribs have a parallel or vertical structure.

It is another object of the present invention to provide the method as defined above, wherein the ribs are connected in an arch shape resulting a structure of a small elastic cup shape such that the MC will collapse into the applicator easily.

It is another object of the present invention to provide the method as defined above, wherein the withdrawal string may further have an elongated tube shape.

It is another object of the present invention to provide the method as defined above, wherein the withdrawal string part is used in order to extract the device from the vaginal cavity.

It is another object of the present invention to provide the method as defined above, wherein the reservoir bag is adapted as a thin membrane which is connected to the ribs in a sealed manner for collecting menstrual fluid.

It is another object of the present invention to provide the method as defined above, wherein the reservoir bag is made of elastic material or non-elastic material.

It is another object of the present invention to provide the method as defined above, wherein the an absorbent element is made from absorbing material selected from a group consisting of: natural fibers, synthetic fibers, fluff pulp, needle-punched engineered absorbents, fiber tows, tow webs, cellulosic sponge materials, superabsorbent materials, materials which forms a gel upon contact with moisture, and combinations thereof.

BRIEF DESCRIPTION

Figure 2:
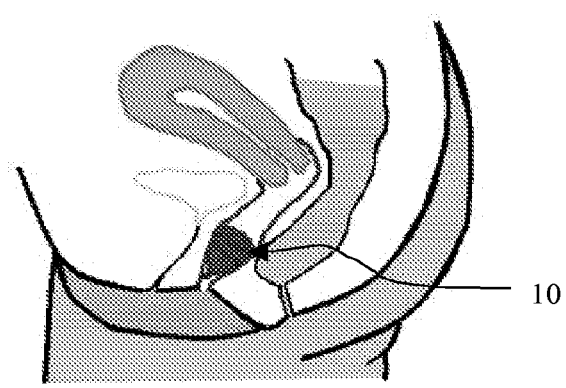
Figure 3:
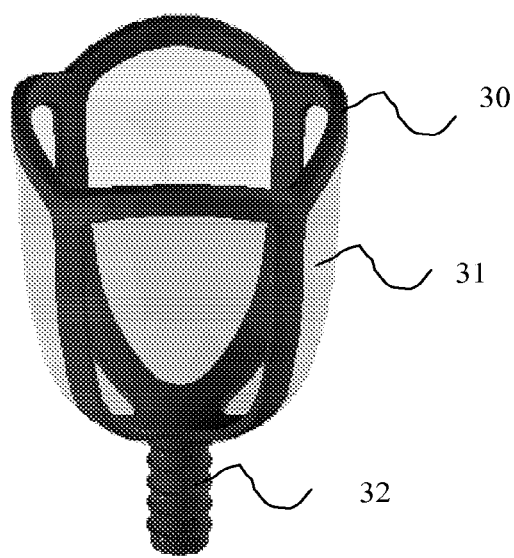

In order to understand the invention and to see how it may be implemented in practice, a few preferred embodiments will now be described, by way of non-limiting example only, with reference to be accompanying drawings, in which:

FIG. 1 is a top view of the disposable catamenial device, in accordance with a preferred embodiment of the present invention, and FIG. 2 is a side view of the disposable catamenial device placed within the vaginal canal, in accordance with a preferred embodiment of the present invention, and FIG. 3 is a semitransparent view illustrating the disposable catamenial device comprising the reservoir bag, in accordance with a preferred embodiment of the present invention

DETAILED DESCRIPTION

The following description is provided so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide device and method pertaining to improved feminine hygiene devices, and more particularly to a vaginal discharge collection device for collecting vaginal discharge.

The present invention presents a disposable catamenial device comprising a menstrual cup having a cup-shape as a barrier worn inside the vagina during menstruation to collect menstrual fluid. The cup collects menstrual fluid and absorbs it.

The present invention provides a disposable catamenial device for the collection of menses discharge of the human female having a menstrual cup (MC) combined with an applicator. FIG. 1 presents a MC comprises: (a) at least three flexible ribs 1a-c extending inwardly from the inner surface of the MC base. The ribs are longitudinally extending ribs affixed to the cup base 3, (b) an elastic rim frame 2 connected in a sealed manner to the top of the ribs 1, (c) a reservoir bag connected to the ribs in a sealed manner for collecting the menstrual fluid. The bag has a pouch like structure attached to the cups ribs 1, (d) a withdrawal string 4 connected to the MC base 3 which enables the extraction of the MC from the vagina. The withdrawal string is positioned within the interior of the MC base.

The disposable catamenial device is merely made of biodegradable materials and further comprises an applicator useful for delivering the MC into the vaginal canal and extracting the MC. Further wherein the bag comprises an absorbent element located along the bag walls preventing spillage or leakage of menses during extraction of the MC, whereby the captured menstrual flow is isolated from the cervix and the vaginal walls. The absorbent material may further contain an antibacterial substance.

The device is flexible and resilient, having a drogue-like structure such that it provides low resistance when inserted and substantial resistance when drawn from the vaginal cavity and allows easier deployment, without problems of dislodgement.

The present invention further presents a MC having a funnel-like structure, a cone-like structure, an umbrella-like structure or any combination thereof.

The MC has a drogue-like structure comprising at least three flexible ribs having an arcuate vertical struts (AVS) structure connected at their proximal ends 5a-c to the elastic rim frame comprising at least three flexible arcuate horizontal struts (AHS), the struts having respective curved portions 6a-c. Distal ends 7a-e of respective struts 1a-c are generally parallel to each other. The AHS has a curvature area less than the curvature area of the AVS allowing easier deployment of the MC resulting in low resistance when inserted and substantial resistance when drawn from the vaginal cavity.

The AVS structure and AHS structure provides additional resilience and semi-automatic deployment of the device to a sealing position within the vagina cavity.

The term "Semi-automatic" refers herein to a rapid and independent deployment of the device within the vagina cavity resulting from its drogue-like structure. The semi-automatic deployment allows the user to position the MC without any manipulation or additional force.

The port of the device of the present invention has a resilient rim having a circular or elliptical shape. The rim is composed of a memory shape alloy coated with soft biodegradable and biocompatible polymer, such as polylactide (PLA) blended with rubber such as ABS polymer. The rim may further be made of a soft memory shape biocompatible and degradable thermoplastic polymers, which changes it's shape at body temperature, such as ϵ-caprolactone. The rim is sealingly connected to the MC as a thin biodegradable and biocompatible polymer which can also be made from PLA.

The present invention further includes an absorbent material which is a polymer located within the bag of the MC. The absorbent material is secured to the MC bag by a non-woven fabric for preventing the dry and the saturated polymer from exiting the MC, while enables the secreted fluid to be absorbed. Thus when the MC is taken out from the vaginal cavity, all secreted liquids remains within the MC cavity.

The present invention further includes a withdrawal chord attached to MC base in a manner in which a user can grasp the downstream end of the string and pull it through the vagina and out for disposal.

The withdrawal string may further be made of T35 ADMIRAL WHTO combed supima cotton thread from Coats North America of Charlotte, N.C.

FIG. 2 illustrates the manner which the MC 10 in position within the vagina cavity of a female human being. The MC is positioned at the end of the vagina and against the cervix so that a seal is established between the MC and the cervix so that all menstrual flow will be captured and retained by the MC.

The present invention improves the known menstrual cup in such a way that it has the advantages of MC with the connivance of a tampon. The MC is disposable, and is inserted to the vaginal cavity by the use of a cardboard applicator.

While the cup is in the applicator, prior to usage, the top rim is bent or folded in such way that when pushed out from the applicator the top rim is opened within the vaginal cavity.

The insertion and the extraction of the MC is performed by using an applicator. By using the applicator there is no need for training and there is no need for the user's fingers to manipulate the MC in the proximity of the vaginal cavity, thereby avoiding important issues of personal hygiene, infection risk, contamination and inconvenience. In addition, the present invention is ecologically friendly since the MC is made mostly of biodegradable materials.

The applicator can be made of plastic, biodegradable material or cardboard. In particular plastic materials such as polyethylene, polypropulene, polyurethane, polyesters, ethylene-vinyl acetate, polystyrene can be used to form the applicator of the present invention. Biodegradable materials which can be used to form the applicator of the invention are for example described in EP 0 606 923 A1, suitable biodegradable materials are for example poly (vinyl alcohol), polyoxyethylene, and the like. The inner cylinder can be formed as a solid or hollow cylinder. In case of a hollow cylinder the recess is formed by two opposite indentations in the rearward end of the wall surface of the inner cylinder.

The MC of the present invention is inserted using an applicator. The applicator comprises two tubular insertion members having hollow cylinder shape while one has a diameter smaller than the other such that the smaller cylinder, the inner sleeve, is inserted into the larger cylinder, the outer sleeve. The open end of the cylinder is inserted through the introitus or opening of the vagina until it is near the top of the vagina and adjacent to the cervix. The cylinder is then withdrawn so that the MC is ejected from the cylinder. The MC then unfolds as an umbrella shape and glides into the end of the vagina (Formix).

The MC may further be coated with lubricant either when it is stored within the applicator or while it is being released from the applicator. The lubricant coating on the device will assist it to slip into place within the vagina.

Reference is now made to FIG. 3, which illustrates catamenial device of the present invention comprising the reservoir bag 31. The bag is connected to the ribs of the MC 30 in a sealed manner for collecting the menstrual fluid. The bag has a pouch like structure attached to the MC ribs, The reservoir bag 31 comprises an absorbent element located along the bag walls preventing spill and leakage during extraction of the MC.

The reservoir bag may be adapted as a thin membrane which is connected to the ribs in a sealed manner for collecting menstrual fluid. The reservoir bag may be made of an elastic material or a non-elastic material.

FIG. 3 further illustrates the structure of the catamenial device of the present invention comprising a withdrawal string 32 connected to the MC base. The withdrawal string may have a tube structure.

The disposable catamenial device for the collection of menses discharge of the female human, complies with FDA regulation pertaining to Obstetrical and Gynecological Devices. The disposable catamenial device is classified to FDA class II performance standards the device further meets FDA biocompatibility standards to prevent adverse tissue reaction.

The absorbent element complies to several absorbency ratings selected from the group consisting of: 6 grams and under, 6 to 9 grams, 9 to 12 grams, 12 to 15 grams or 15-18 grams.

There is provided in accordance with a preferred embodiment a method of manufacturing a disposable catamenial device comprising the steps of:

(a) molding at least three longitude arch-like ribs made of flexible material in a drogue configuration to a flat base, (b) molding the ribs to at least three horizontal arcuate struts resulting a port having a resilient rim for leading menstrual flow discharged from the cervix to pass through the cup, (c) attaching a bag comprising an absorbent material, (d) contacting the drogue and the bag so as to define an intra vaginal reservoir for receiving and containing menstrual flow that enters the reservoir through the port, and (e) fusing the bag to the drogue like ribs, (f) attaching a withdrawal string to the flat base.

The molding ribs results arcuate vertical struts (AVS) structure connected to a flat base, the ribs connected with elastic rim frame comprising at least three flexible arcuate horizontal struts (AHS), further wherein the AHS has a curvature less than the curvature of the AVS allowing easier deployment of the MC resulting in low resistance when inserted and substantial resistance when drawn from the vaginal cavity.

There is provided in accordance with a preferred embodiment of the present invention a method of capturing and containing the menstrual flow of a female human being comprising the steps of: (a) providing a disposable catamenial device for the collection of menses discharge of the human female comprising: a menstrual cup (MC), comprising: (i) at least three resilient ribs extending inwardly from the inner surface of the MC base, (ii) an elastic rim frame connected to the top of the ribs, (iii) a reservoir bag connected to the ribs in a sealed manner for collecting the menstrual fluid, and (iv) a withdrawal string connected to the cup bottom for enabling the extraction of the MC from the vagina.

(b) providing an applicator, (c) placing in an end of an applicator the disposable catamenial device, (d) inserting the end of the applicator into the vagina, (e) releasing the device from the end of the applicator whereby the device automatically seats itself within the vagina cavity, and (f) withdrawing the applicator from the vagina, There is further provided in accordance with a preferred embodiment of the present invention the method as defined above, wherein the rim functions as a spring such that when ejected outside the applicator, the rim returns to its original shape and the MC is opened within the potential vaginal cavity.

There is further provided in accordance with a preferred embodiment of the present invention the method as defined above, wherein the rim resilient structure and elasticity enables the MC to be positioned with in the vagina in a sealed manner such that the MC comprising the collected fluid is held inside the vagina.

There is further provided in accordance with a preferred embodiment of the present invention the method as defined above, wherein the rim is formed of an injection molded thermoplastic rubber.

There is further provided in accordance with a preferred embodiment of the present invention the method as defined above, wherein the device for containing menstrual flow of a female human structure provides an additional spring-like resilience for facilitating semi-automatic deployment of the device to a sealing position within the vagina cavity.

There is further provided in accordance with a preferred embodiment of the present invention the method as defined above, wherein the MC has a drogue-like structure such that it provides substantial resistance when dragged from the vagina cavity and allows easier deployment.

There is further provided in accordance with a preferred embodiment of the present invention the method as defined above, wherein the MC may further have a funnel-like structure, a cone-like structure, an umbrella-like structure or any combination thereof.

There is further provided in accordance with a preferred embodiment of the present invention the method as defined above, wherein the reservoir is collapsible so as to be substantially enclosed within the rim during use.

There is further provided in accordance with a preferred embodiment of the present invention the method as defined above, wherein the applicator comprises two tubular insertion members having hollow cylinder shape while one has a diameter smaller than the other such that the smaller cylinder is inserted into the larger cylinder.

There is further provided in accordance with a preferred embodiment of the present invention the method as defined above, wherein the ribs have a parallel or vertical structure.

There is further provided in accordance with a preferred embodiment of the present invention the method as defined above, wherein the ribs are connected in an arch shape resulting a structure of a small elastic cup shape such that the MC will collapse into the applicator easily.

There is further provided in accordance with a preferred embodiment of the present invention the method as defined above, wherein the withdrawal string may further have an elongated tube shape.

There is further provided in accordance with a preferred embodiment of the present invention the method as defined above, wherein the withdrawal string part is used in order to extract the device from the vaginal cavity.

There is further provided in accordance with a preferred embodiment of the present invention the method as defined above, wherein the reservoir bag is adapted as a thin membrane which is connected to the ribs in a sealed manner for collecting menstrual fluid.

There is further provided in accordance with a preferred embodiment of the present invention the method as defined above, wherein the reservoir bag is made of elastic material or non-elastic material.

There is further provided in accordance with a preferred embodiment of the present invention the method as defined above, wherein the absorbent element is made from absorbing material selected from a group consisting of: natural fibers, synthetic fibers, fluff pulp, needle-punched engineered absorbents, fiber tows, tow webs, cellulosic sponge materials, superabsorbent materials, materials which forms a gel upon contact with moisture, and combinations thereof.

The present invention provides method of manufacturing a device for containing menstrual flow of a female human which complies with cGMP and QS (quality systems).

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A catamenial device configured for the collection of menses discharge of a human female, comprising: a flexible resilient menstrual cup (MC), comprising:
   a rib structure extending from a distal open end of said device toward a proximal end of said device; and
   a reservoir bag connected to said rib structure for collecting the menses discharge, said reservoir bag having an open distal end and a proximal end, wherein said reservoir bag proximal end and said rib structure proximal end overlap;
   wherein said device has a cylindrical body tapering proximally;
   wherein said device is radially symmetric about a central axis, from said device proximal end to said device distal end;
   wherein said MC has a port about the central axis at said device distal end, said rib structure configured to seal said device distal end at said port to a vaginal cavity of the human female, at a location along the vaginal cavity which is remote from the cervix.

2. The device according to claim 1, wherein said rib structure resilient structure and elasticity enables said MC to be positioned within the vaginal cavity in a sealed manner such that said MC comprising the collected fluid is held inside the vaginal cavity.

3. The device according to claim 1, wherein said rib structure has one of a parallel structure, a vertical structure, and an elongate structure.

4. The device according to claim 1, wherein said reservoir bag includes a thin membrane which is made from elastic or non-elastic material.

5. The device according to claim 1, additionally comprising at least one absorbent element located along walls of said reservoir bag, said at least one absorbent element configured to prevent spill and leakage during extraction of said MC.

6. The device according to claim 1, wherein said at least one absorbent element is made from absorbing material selected from a group consisting of: natural fibers, synthetic fibers, fluff pulp, needle-punched engineered absorbents, fiber tows, tow webs, cellulosic sponge materials, superabsorbent materials, materials which forms a gel upon contact with moisture, and combinations thereof.

7. The device according to claim 1, wherein said device complies with at least one of FDA regulations pertaining to Obstetrical and Gynecological Devices; FDA class II performance standards; and FDA biocompatibility standards for prevention of adverse tissue reaction.

8. The device according to claim 1, wherein said rib structure is configured to collapse into the applicator.

9. The device according to claim 1, wherein said rib structure includes biodegradable materials.

10. The device according to claim 1, wherein said MC has a drogue-like structure such that it allows deployment within the vaginal cavity and resists inadvertent retraction from within the vaginal cavity.

11. The device according to claim 1, wherein said MC has one of a cone-like structure, an umbrella-like structure, and a combination thereof.

12. The device according to claim 1, wherein said rib structure includes at least a sine-shaped rib.

13. The device according to claim 1, further comprising an elastic rim frame connected to said rib structure at a distal end of said device, said elastic rim frame including one of at least two flexible arcuate struts and at least two circumferentially arranged struts.

14. The device according to claim 1, wherein said reservoir bag is connected to said elastic rim frame.

15. The device according to claim 1, wherein said device is disposable.

16. The device according to claim 1, wherein said central axis is configured to be coincidental with a vaginal axis of the female human.

17. The device according to claim 1, wherein said rib structure includes a plurality of ribs, all of said ribs being convex.

18. The device according to claim 1, wherein said rib structure includes a plurality of ribs, all of said ribs having a same shape and length.

19. The device according to claim 1, wherein said rib structure includes a plurality of ribs, all of said ribs being curved and being parallel to each other at their distal ends.

20. The device according to claim 1, wherein said rib structure is outwardly resilient when in a resting state.

21. The device according to claim 1, wherein said port is configured to seal said device at a vaginal passageway leading to the cervix, at a distance from the cervix.

22. The device according to claim 1, wherein said port is configured to seal said device against inner walls of a vaginal passageway, at a location along the vaginal passageway which is remote from a cervix.

23. The device according to claim 1, wherein said rib structure includes a plurality of ribs connected to each other in an arch shape.

24. The device according to claim 1, wherein said rib structure is configured to open said MC into a cup shape.

25. The device according to claim 1, wherein said device terminates in said port at said device distal end, said port configured to seal said device distal end to the vaginal cavity of the human female.

26. The device according to claim 1, wherein said rib structure central axis is configured to be coincidental with a central axis of the vaginal cavity.

27. The device according to claim 1, wherein said device distal end is an elastic rim of said device.

28. The device according to claim 1, wherein said rib structure is configured to apply forces at said device distal end, wherein said forces are evenly distributed about said device distal end.

29. The device according to claim 1, wherein said rib structure includes ribs which have a parallel structure along at least a portion of said ribs.

30. The device according to claim 1, wherein said MC does not narrow from said device distal end to said device proximal end.

31. The device according to claim 1, wherein said rib structure is radially symmetric about a central axis, from said device proximal end to said device distal end.

32. The device according to claim 1, wherein said device distal open end is perpendicular to the central axis.

* * * * *